(12) United States Patent
Leiner et al.

(10) Patent No.: US 8,172,812 B2
(45) Date of Patent: May 8, 2012

(54) SYRINGE FOR THE METERED DELIVERY OF MATERIALS, IN PARTICULAR OF DENTAL MATERIALS

(75) Inventors: Uwe Leiner, Midlum (DE); Manfred Thomas Plaumann, Cuxhaven (DE)

(73) Assignee: Voco GmbH, Cuxhaven (DE)

( * ) Notice: Subject to any disclaimer, the term of this patent is extended or adjusted under 35 U.S.C. 154(b) by 418 days.

(21) Appl. No.: 11/864,031

(22) Filed: Sep. 28, 2007

(65) Prior Publication Data
US 2008/0125723 A1  May 29, 2008

(30) Foreign Application Priority Data
Sep. 28, 2006 (DE) .................... 20 2006 014 996 U

(51) Int. Cl.
*A61M 5/315* (2006.01)

(52) U.S. Cl. ........ 604/227; 604/208; 604/211; 604/218; 433/80

(58) Field of Classification Search .................. 604/187, 604/207, 208, 209, 211, 218, 224, 227; 433/80, 433/81, 89, 90; 222/390
See application file for complete search history.

(56) References Cited

U.S. PATENT DOCUMENTS

| | | | |
|---|---|---|---|
| 3,853,125 A | 12/1974 | Clark et al. | |
| 4,863,072 A * | 9/1989 | Perler | 222/390 |
| 5,599,314 A * | 2/1997 | Neill | 604/207 |
| 5,697,918 A | 12/1997 | Fischer et al. | |
| 6,571,992 B2 * | 6/2003 | Pierson et al. | 222/390 |
| 7,077,826 B1 * | 7/2006 | Gray | 604/171 |
| 2003/0036762 A1 * | 2/2003 | Kerr et al. | 606/93 |
| 2005/0209571 A1 * | 9/2005 | McKay | 604/227 |
| 2005/0222539 A1 | 10/2005 | Gonzales et al. | |
| 2007/0072146 A1 * | 3/2007 | Pierson | 433/90 |

FOREIGN PATENT DOCUMENTS

| | | |
|---|---|---|
| DE | 42 00 044 | 9/1992 |
| DE | 699 22 027 | 10/2005 |
| EP | 0472023 A1 | 2/1992 |

OTHER PUBLICATIONS

German Search Report for Application 20 2006 014 996.1 dated Apr. 18, 2007.

* cited by examiner

*Primary Examiner* — Kevin C Sirmons
*Assistant Examiner* — Emily Schmidt
(74) *Attorney, Agent, or Firm* — Banner & Witcoff, Ltd.

(57) ABSTRACT

A syringe for the metered delivery of materials, in particular of dental materials, is described. The syringe may include a tube which accommodates material and a rotary plunger. Radially extending gripping bodies may be disposed about a longitudinal axis of the syringe are disposed on the syringe in the region of the outlet opening of the tube for applying the fingers of the hand for rotating the tube about the rotary plunger.

16 Claims, 4 Drawing Sheets

SYRINGE FOR THE METERED DELIVERY OF MATERIALS, IN PARTICULAR OF DENTAL MATERIALS

Figure 1:
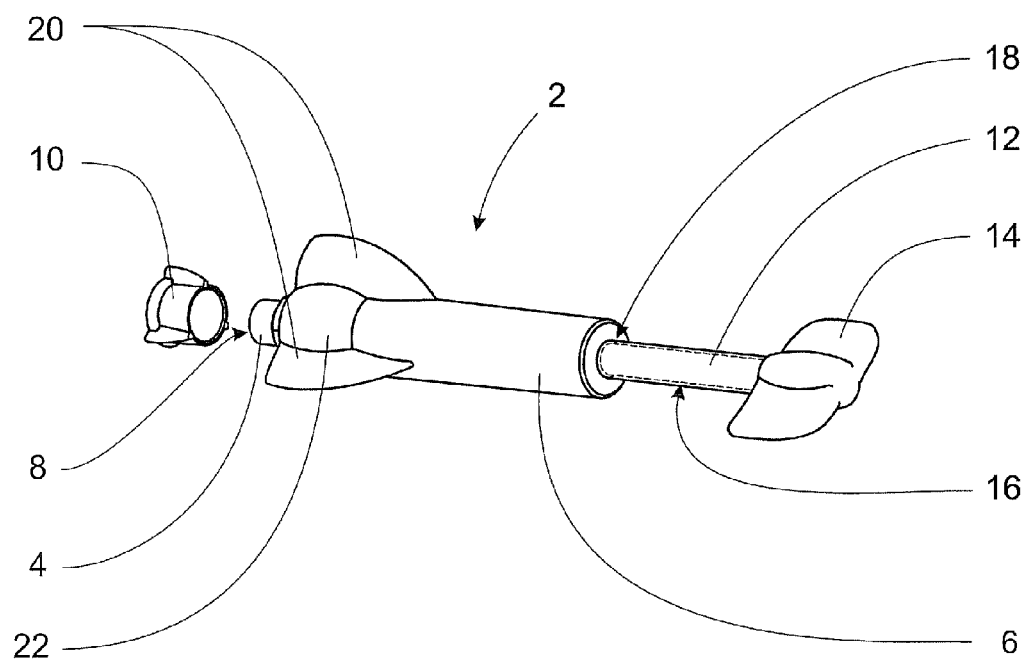

The present invention relates to a syringe for the metered delivery of materials, in particular of dental materials, with a tube which accommodates material and a rotary plunger which can be introduced into the tube.

A syringe of this kind is known, for example, from DE 4 332 307 C1. Here the material which is to be delivered is located in a cartridge into which a rotary plunger plunges from one end and presses against a displaceable inner stopper which adjoins the material. The quantity of delivered material can be easily and precisely metered through the angle of rotation or the number of revolutions of the rotary plunger.

Two hands are required in order to operate a syringe of this kind. After removing a closing stopper from the outlet opening, one hand grips the cartridge which comprises the material directly or by means of a gripping piece which is flange-mounted on this cartridge. The outlet opening is directed at an appropriate instrument which, in the case of the dental material, may be a spatula, for instance, which serves to receive the sensitive material. The material is expelled from the cartridge through the outlet opening by rotating the rotary plunger with the other hand. According to the number of revolutions of the rotary plunger, a greater or smaller amount of material is expelled from the cartridge. The material quantity can therefore easily be metered without wasting excess material.

There are numerous proven embodiments of this kind of syringe which can be used for the most varied pasty materials and in this respect have different advantages and disadvantages. However it has become apparent when handling these syringes that the required two-handed operation is disadvantageous as regards metering. A particular disadvantage lies in the operation of these syringes when delivering dental materials. The material can only be delivered to an auxiliary appliance, which must either be held by a third hand or deposited on a sterile surface which is suitable for this. The syringe must be regularly deposited and the auxiliary appliance gripped after the material has been delivered. If too little material has been metered to the auxiliary appliance, the syringe must be deposited and the auxiliary appliance embraced again. In the case of a dental treatment the space conditions directly at the treatment location are often cramped and little deposit surface is available, which makes depositing and embracing or the employment of an assistant inconvenient.

The object of the present invention is therefore to reduce or to eliminate the above-mentioned disadvantage and to provide a syringe for the metered delivery of materials, in particular dental materials, which is easy to produce, can be operated with just one hand and yet at the same time enables the quantity of material which is to be delivered to be accurately and reliably metered.

The invention achieves the object by proposing a syringe for the metered delivering of materials, in particular of dental materials, with a tube which accommodates materials and a rotary plunger which can be introduced into the tube and has a contact body for applying to the palm of a hand, wherein the tube comprises an outlet opening which is disposed opposite the point of entry of the rotary plunger, and wherein three or four (no more, for ergonomic reasons preferably three) radially extending gripping bodies disposed symmetrically about a longitudinal axis of the syringe are disposed on the syringe in the region of the outlet opening of the tube for applying the fingers of the hand, wherein the gripping bodies have a radial height of 0.5 cm or more.

When operating the syringe according to the invention the contact body of the rotary plunger is placed in the palm of the hand and the tube with the three or four gripping bodies which accommodates the material is gripped with the fingers of the same hand. Gripping is usually carried out with the thumb, the index finger and the middle finger, the thumb and the index finger being placed against two of the gripping bodies and the middle finger being placed on the tube. The tube is rotated through a specific angle relative to the rotary plunger, which lies in a stationary manner in the palm, by appropriately moving the thumb and the index finger in the direction of rotation. The rotary plunger then penetrates to an increasing degree into the tube and conveys the material through the outlet opening to the outside.

The syringe according to the invention has advantages over known syringes, as the material can be delivered in a reliable and metered manner by operating the syringe with one hand. On account of the very large radial height of the gripping bodies of 0.5 cm or more, a sufficiently high torque can also be applied via the finger-tip, e.g. of the thumb, when a highly viscous material is to be extruded from the syringe. There is no need for the auxiliary appliance which receives the material to be deposited or the appliance held by an assistant, as the second hand of the user is available for holding the auxiliary appliance. Therefore neither an additional helping hand nor an additional deposit surface is necessary.

According to the invention, the three or four gripping bodies are disposed symmetrically (at an angular spacing of 120° or 90°) about a longitudinal axis of the syringe according to the invention. Therefore at least one gripping body can be reached with the fingers without an embracing action and in an invariable manner from any desired angle of rotation, and the one-handed rotation of the tube relative to the rotary plunger is simplified.

The gripping bodies are preferably substantially in the form of a wing, the height of which, according to the invention, is 0.5 cm or more, i.e. it corresponds approximately to half the width of a finger or more, so that they can easily be configured according to the ergonomic requirements and guarantee a secure grip with a small overall volume.

The disposal of a respective depression at the surfaces of the gripping bodies pointing opposite to the preferred direction of rotation for applying a finger is particularly ergonomic. The hold of the fingers operating the syringe according to the invention becomes more secure as a result and the fingers are prevented from slipping, even in the case of highly viscous materials which require a relatively high torque for the delivery.

The rotary plunger preferably comprises a first thread which corresponds with a second thread in another component of the syringe according to the invention. The interaction of two threads for screwing the rotary plunger into the tube enables the position of the rotary plunger in relation to the tube and therefore the quantity of material which is delivered to be precisely metered. The syringe according to the invention can be manufactured for each purpose and the material quantities which are to be expected for this through an appropriate choice of thread pitch. The shallower the thread pitch, the smaller the material quantities which can be metered highly accurately by rotating the rotary plunger and the smaller the torque which is to be applied to deliver the, for example, highly viscous dental material.

It is in many cases of advantage to provide an outer tube which at least partly encloses the tube which accommodates material. The syringe can be made more attractive visually by concealing the purely functional (inner) tube which accommodates the material. In the case of light-sensitive materials in an (inner) tube dyed black, for example, the syringe according to the invention becomes more aesthetic as a whole by using a more tasteful outer tube of any desired colour.

The outer tube which is used is preferably pressed, screwed or welded to the tube which accommodates the material, so that a torque which is applied to the outer tube is transmitted directly to the tube. The outer tube and the tube could optionally be positively connected together in an equally favourable manner by a snap mechanism with protuberances and recesses disposed at the tubes.

The disposal of the second thread in the tube which accommodates the material at the end which is remote from the outlet opening is of particular advantage, as a further component is eliminated.

If an outer tube is used, it is in addition favourable to dispose the second thread at the outer tube at the end which is remote from the outlet opening. It is as a result possible to eliminate a thread at the replaceable (inner) tube.

When using a syringe according to the invention for light-sensitive materials (e.g. dental filling material) which are irradiation-cured or similar, it is of advantage to use a tube which is impervious to light and is preferably of a black colour. Light incidence can be excluded and the material which is to be delivered can be stored for longer as a result.

It is favourable to configure the gripping bodies or one or more surface(s) disposed in the region of the gripping bodies so that the syringe can be deposited on a plane deposit surface so that the longitudinal axis of the syringe rises towards the outlet opening. The outlet opening of the syringe being used can as a result be kept clean and sterile when the latter is deposited for a short time and there is a possibility of material residues projecting out of the outlet opening, as the outlet opening is held safely in the air and does not contact the deposit surface.

The production costs of a syringe according to the invention are particularly favourable when it is made of one or more different plastics material(s). After preparing casting moulds for the syringe components, series production takes place quickly and with low material costs.

It is in this respect of advantage for the rotary plunger to be made of acrylonitrile-butadiene-styrene and for the second thread to be disposed in a component which is made of polyamide. The thread friction is decreased and the torque applied by the user to the rotary plunger is converted particularly well into a translatory movement into the tube as a result.

Starting out from the feature of one-handed operability, it is particularly preferable for the overall length of the syringe according to the invention to lie in a range from 80 mm to 160 mm. The overall length is in this respect defined as the maximum dimension of the syringe along its longitudinal axis, i.e. the maximum measurement between the outlet opening and the contact body of the rotary plunger. A dimension outside of this range renders a one-handed operation more difficult or impossible.

In a particularly preferred embodiment the syringe according to the invention contains a dental material, e.g. a filling material. The syringe according to the invention is particularly suitable for use in dental operations.

Figure 2:
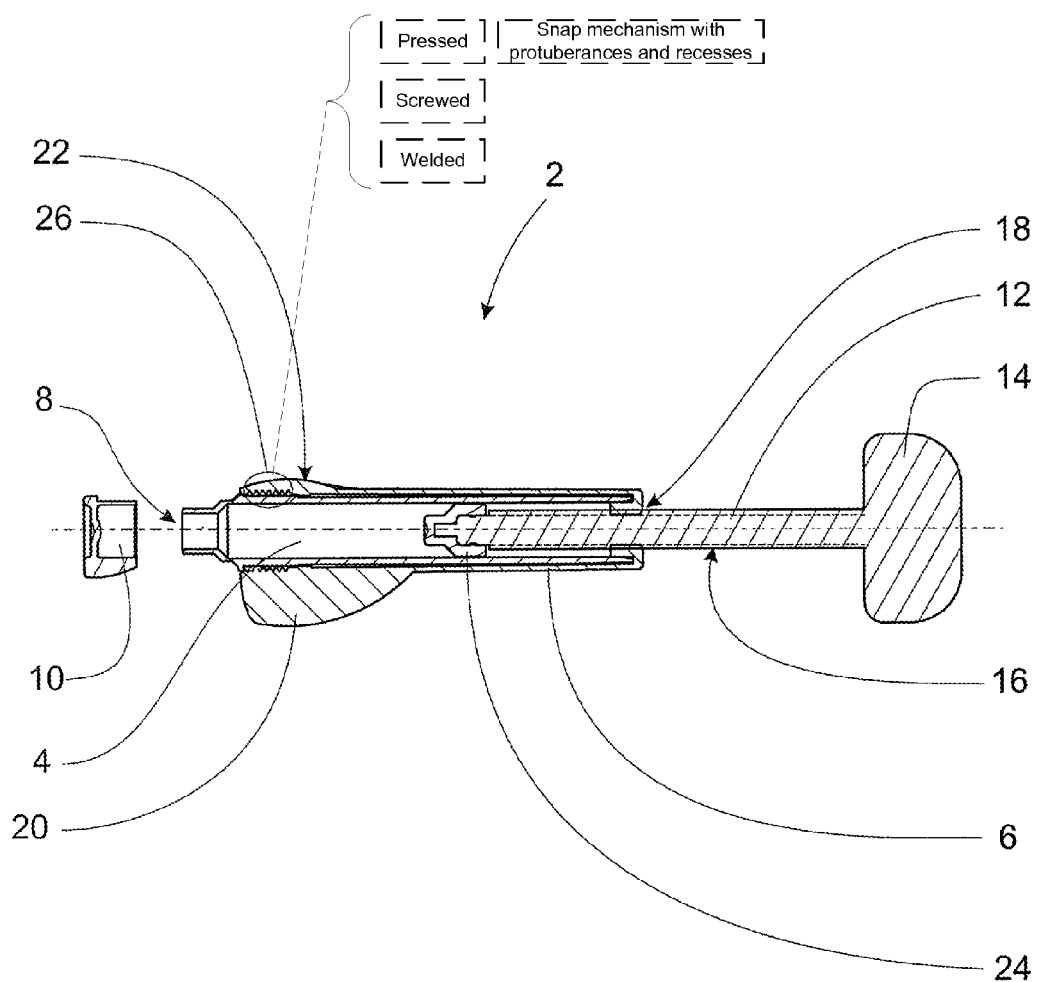
Figure 3:
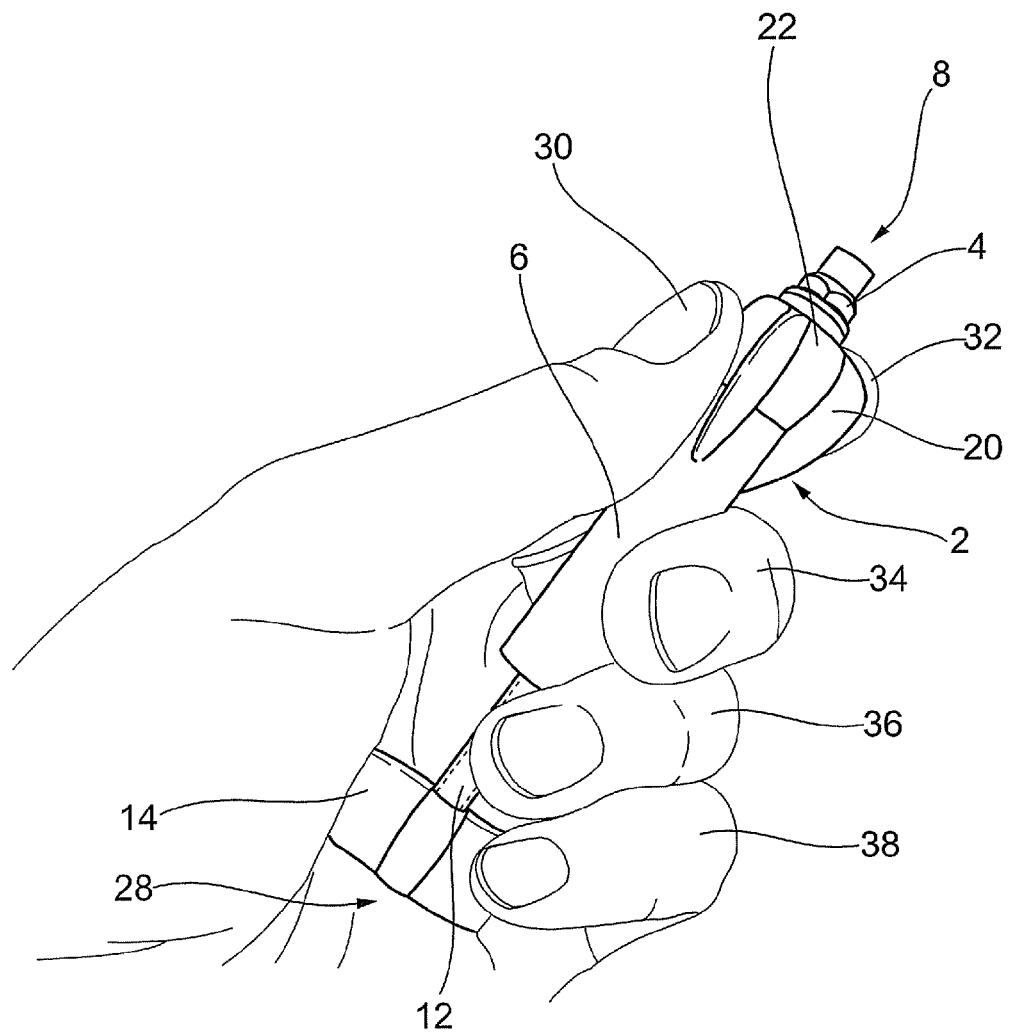
Figure 4:
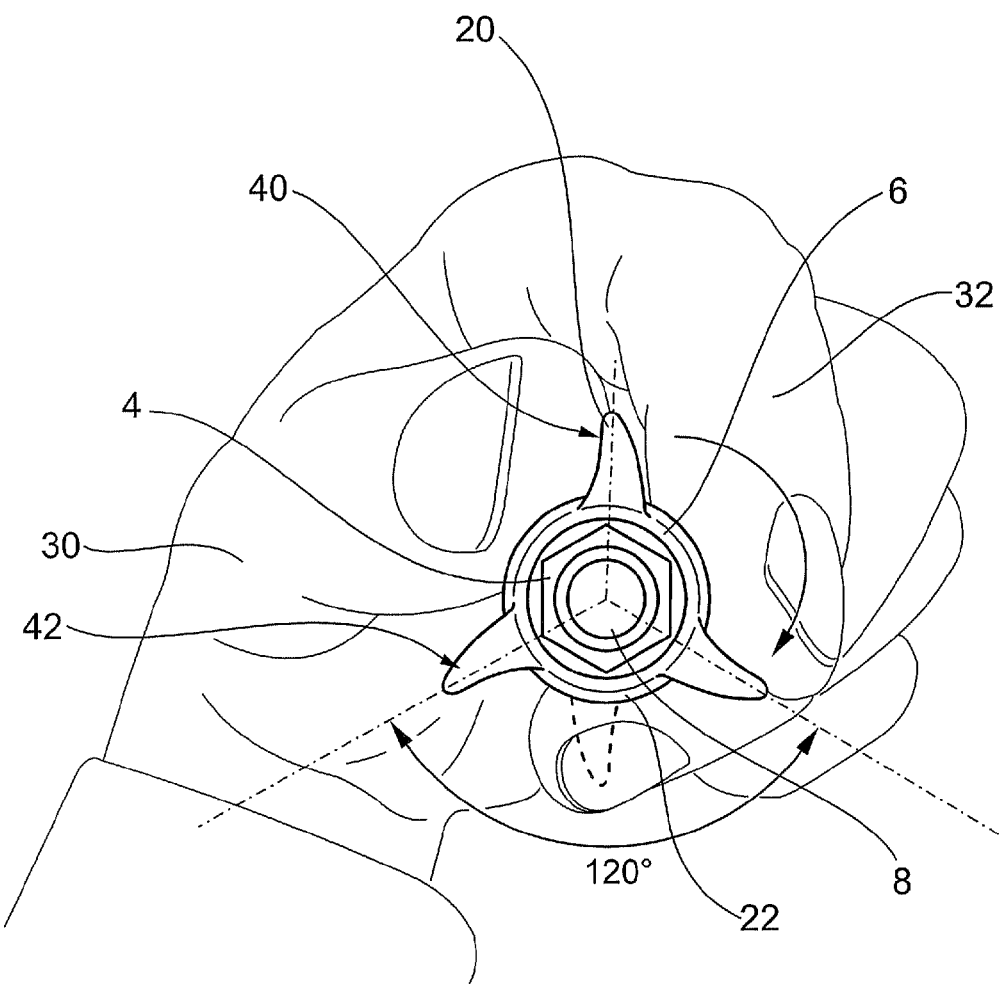

The invention is illustrated in detail in the following on the basis of the figures, in which identical reference characters designate the same elements and in which:

FIG. 1: is a three-dimensional view of the syringe according to the invention,

FIG. 2: is a lateral longitudinal section of the syringe according to the invention, FIG. 3: shows the syringe according to the invention in a hand and FIG. 4: is a detail view of the gripping bodies with applied fingers.

A special embodiment of the invention is shown in the three-dimensional view of FIG. 1. The syringe 2 comprises a tube 4 which is filled with the material to be delivered and almost completely enclosed by an outer tube 6. The end of the tube 4 which projects out of the outer tube 6 comprises an outlet opening 8 which can be closed by a closing stopper 10 for protecting the material. A rotary plunger 12 projects out of the end of the outer tube 6 which lies opposite the outlet opening 8, which plunger comprises a wing- or double-wing-like contact body 14 at its end which is remote from the tubes 4, 6 for applying to the palm of a hand. The rotary plunger 12 also comprises an external thread 16, which is merely indicated in FIG. 1 and corresponds with an internal thread 18, which is likewise merely indicated, the internal thread 18 being disposed in the outer tube 6, although it could alternatively be disposed in the tube 4.

Two gripping bodies 20 are located on the outer tube 6 in the region of the outlet opening 8, i.e. the side which is remote from the rotary plunger 12. It is to be noted that a third gripping body 20 cannot be seen in this view as it is concealed by the syringe 2. The gripping bodies 20 have a preferred, particularly aesthetic wing form. However the gripping bodies 20 can be formed in a different way and need not necessarily have the wing form which is shown. It is of course in any case appropriate to form the gripping bodies 20 according to ergonomic criteria, so that they can be brought particularly well into contact with a thumb and an index finger. According to FIG. 1, the gripping bodies 20 are disposed at an angle of 120° relative to one another and essentially serve to rotate the outer tube 6 in relation to the rotary plunger 12.

The gripping bodies 20 also serve to deposit the closed or open syringe 2 on a deposit surface without the outlet opening 8 contacting the deposit surface. For this purpose the heights of the gripping bodies in relation to the outer tube 6 are of sufficiently large dimensions so that the syringe 2 lies on the outermost ends of the gripping bodies 20 and the opening 8 of the tube 4 is disposed distinctly above the deposit surface when the syringe is laid down. This function could alternatively or additionally be provided by an arched region 22 between the gripping bodies 20 whose maximum radius is greater than that of the outer tube 6. The rotary plunger 12 preferably comprises a flat, for example double-wing contact body 14, so that the contact body 14 can lie as flatly as possible on the deposit surface and the deposited syringe rises in the direction of the delivery side.

According to FIG. 1, the region 22 between the gripping bodies 20 has a convex surface curvature which improves the handling properties of the syringe 2 in parallel with the function described above and is also visually attractive. Moreover, this convex region 22 provides a volume which may be of advantage for establishing the connection between the outer tube 6 and the tube 4 and is described in the following on the basis of FIG. 2.

FIG. 2 shows somewhat more clearly the structure of the syringe 2 in a longitudinal sectional drawing in an exemplary operating state. The cartridge-like (inner) tube 4 is enclosed by the outer tube 6 and projects out of the outer tube 6 at the end which lies opposite the rotary plunger 12 and bears the gripping bodies 20. The rotary plunger 12 is located with the end which is opposite the contact body 14, for example, in the centre of the tube 4 and comprises a stopper 24. This representation corresponds to a tube 4 which is half-empty.

If the tube 4 is rotated relative to the rotary plunger 12, which is placed in a palm and therefore stationary, the tube 4 executes a translatory movement relative to the rotary plunger 12 parallel to the longitudinal axis of the syringe 2. If the direction of rotation is correct, the stopper 24 is then pushed in the direction of the outlet opening 8 and expels the material located in the tube 4 from the outlet opening 8. According to the number of revolutions or according to the angle of rotation, the free volume in the tube 4 is reduced by a specific degree which corresponds to the delivered material quantity. The ratio between the angle of rotation and the delivered material quantity is directly dependent on the flank pitch of the threads 16 and 18. Very small material quantities can be accurately metered when the flanks are very shallow, while a greater material throughput is more likely to be obtained with large flank pitches.

When the syringe 2 is operated with one hand, forces which are to enable the tube 4 to rotate about the rotary plunger 12 are transmitted via the gripping bodies 20 to the outer tube 6. For this purpose it is necessary for the forces which are introduced via the gripping bodies 20 to be reliably transmitted to the tube 4. This takes place through a sufficiently durable connection between the tube 4 and the outer tube 6 which can be achieved, for example, by means of a positive fit. According to FIG. 2, the tube 4 is screwed to the outer tube 6 via mating threads 26 in the convex region 22. It is in this respect of advantage for the flank pitch of the mating threads 26 to extend opposite to the pitch of the threads 16 of the rotary plunger and 18 of the thread corresponding therewith in the outer tube 6, so that the connection between the tube 4 and the outer tube 6 is additionally secured by screwing in the rotary plunger 12. As an alternative to this, the connection between the outer tube 6 and the tube 4 can be effected by a non-positive fit. A further method for securing the connection is a positive fit, which is achieved by applying protuberances to the (inner) tube 4 and recesses corresponding with the protuberances to the outer tube 6. These may be applied, for example, in the region of the outlet opening 8.

The torque which is produced by rotating the outer tube 6 relative to the rotary plunger 12 can be reduced by using a suitable material combination between the rotary plunger 12 and the outer tube 6. The combination of acrylic-butadiene-styrene (ABS) and polyamide (PA) has in particular proved to be suitable.

According to FIG. 3, the syringe 2 is placed without a closing cap 10 in a hand, with the contact body 14 lying on the palm 28, just above the ball of the thumb. The outer tube 6 is held at the gripping bodies 20 by the thumb 30 and by the index finger 32, and the middle finger 34 as well as the ring finger 36 lie loosely on the outer tube 6 or additionally stabilise the position through slight pressure in the direction of the palm 28. On account of the compact dimensions of the syringe 2, the little finger 38 does not automatically contact the syringe 2 in this embodiment.

In order to deliver the material in a metered manner from the tube 4 through the outlet opening 8, the rotary plunger 12 is held in the palm 28 so as to be non-rotatable in relation to the hand and the outer tube 6 is rotated clockwise by moving the thumb 30 out of the plane of the drawing and the index finger 32 into the plane of the drawing. This causes the rotary plunger 12 to move further into the outer tube 6 or the tube 4, whereby the volume which is available inside the tube 4 for the material is reduced, so that material emerges from the outlet opening 8. The quantity of material which is to be delivered can be accurately metered by selecting the angle of rotation of the outer tube 6 about the rotary plunger 12.

The gripping bodies 18 are accurately configured on the basis of ergonomic and aesthetic criteria. FIG. 4 shows the cross section of the syringe 2 on the delivery side with three gripping bodies 20 which are staggered by 120° and adjoin the convex region 22. A possible exemplary cross section of the gripping bodies 20 with the thumb 30 and the index finger 32 engaged is shown in this representation. Here the thumb 32 lies on a gripping body 20 whose surface 40 which faces the thumb has a concave curvature which can be formed as a depression over the entire surface 40. This results in an ergonomically favourable form in which the thumb 30 rests particularly well and without slipping. The surface 42 of the gripping body 20 which points towards the thumb 30 and is spaced apart from the thumb 30 has a convex curvature which is attractive (solely) for aesthetic reasons. Finally, if the syringe 2 is correctly used, this surface 42 should not absorb any force directed towards it, so that a concave curvature is technically not necessary.

As represented in FIG. 4, the gripping bodies 20 are disposed at an angle of 120° relative to one another and therefore symmetrically relative to the longitudinal axis of the syringe 2. The angle of 120° is appropriate when using the thumb 30 and index finger 32 to operate the syringe, for this angle can very easily be taken up between the finger-tip surfaces. Three gripping bodies 20 are preferably disposed on the syringe 2 in the manner shown. However an embodiment of the syringe 2 with four gripping bodies 20 at an angle of 90° relative to one another is also conceivable, this making a one-handed operation easy.

The direction of rotation which is required for this embodiment is the clockwise direction, so that the thumb 30 must move upwards in the plane of the drawing and the index finger downwards so that the tube 4 and the outer tube 6 move in the direction of the rotary plunger 12 in order to deliver material from the outlet opening 8.

The present invention enables material to be delivered in a metered manner from a syringe by one-handed operation. The syringe which is represented in the figures and the description is only to be understood as an embodiment. Possible forms of syringes are any in which a rotary plunger can be placed in a stationary manner in a palm so that when a tube with material to be delivered is rotated, material can be delivered in a metered manner with the same hand. An outer tube and a wing-like form of gripping bodies are not specified according to the invention.

The invention claimed is:

1. A syringe for the metered delivery of materials, comprising:
   a tube which accommodates the material; and
   a rotary plunger which can be introduced into the tube and has a contact body configured to be applied to a palm of a hand,
   wherein the tube has an outlet opening which is disposed opposite the point of entry of the rotary plunger, and
   wherein at least three radially extending gripping bodies disposed symmetrically about a longitudinal axis of the syringe are disposed on the syringe at the outlet opening of the tube, the at least three radially extending gripping bodies being configured to receive fingers of said hand while the rotary plunger is applied to the palm of said hand, said tube being configured to rotate about the rotary plunger via force from said fingers, wherein the gripping bodies have a radial height of 0.5 cm or more.

2. A syringe according to any one of the preceding claims, wherein the gripping bodies are in each case substantially in the form of a wing.

3. A syringe according to claim 1, wherein the gripping bodies each includes a depression for applying a finger at a surface pointing opposite to a preferred direction of rotation.

4. A syringe according to claim 1, with an outer tube which at least partly encloses the tube which accommodates the material.

5. A syringe according to claim 4, wherein the tube and the outer tube are pressed, screwed or welded together.

6. A syringe according to claim 5, wherein the tube and the outer tube are positively connected together by a snap mechanism with protuberances and recesses disposed at the tubes.

7. A syringe according to claim 1, wherein the rotary plunger includes a first thread which corresponds with a second thread in another component of the syringe.

8. A syringe according to claim 7, wherein the other component is the tube which accommodates the material, and the second thread is disposed at the end of the tube which is remote from the outlet opening.

9. A syringe according to claim 7, wherein the other component is an outer tube, wherein the second thread is disposed at the end which is remote from the outlet opening.

10. A syringe according to claim 1, wherein the tube is impervious to light and is preferably of a black colour.

11. A syringe according to claim 1, wherein the gripping bodies or one or more surfaces disposed in the region of the gripping bodies are configured so that the syringe can be deposited on a plane deposit surface so that the longitudinal axis of the syringe rises towards the outlet opening.

12. A syringe according to claim 1, wherein the syringe is made of one or more different synthetic materials.

13. A syringe according to claim 12, wherein the rotary plunger is made of acrylonitrile-butadiene-styrene and the second thread is disposed in a component which is made of polyamide.

14. A syringe according to claim 1, wherein the overall length of the syringe lies in a range from 80 mm to 160 mm.

15. A syringe according to claim 1, wherein the tube contains a dental material.

16. A syringe according to claim 1, wherein the syringe includes four radially extending gripping bodies.

\* \* \* \* \*